United States Patent [19]

Petersen et al.

[11] Patent Number: 4,631,285
[45] Date of Patent: Dec. 23, 1986

[54] β-CARBOLINE-3-CARBOXYLIC ACID DERIVATIVES, AND THEIR USE AS PSYCHOTROPIC AGENTS

[75] Inventors: Erling N. Petersen, Glostrup; Leif H. Jensen, Hellerup; Frank Watjen, Bajsvaerd, all of Denmark; Dieter Seidelmann, Berlin, Fed. Rep. of Germany

[73] Assignee: Schering Aktiengesellschaft, Berlin and Bergkamen, Fed. Rep. of Germany

[21] Appl. No.: 734,222

[22] Filed: May 15, 1985

[30] Foreign Application Priority Data

May 15, 1984 [DK] Denmark ............................ 2401/84

[51] Int. Cl.[4] .................. A61K 31/395; C07D 471/04
[52] U.S. Cl. ...................................... 514/292; 546/86
[58] Field of Search .................................. 546/85, 86

[56] References Cited

U.S. PATENT DOCUMENTS 3,202,667 8/1965 Szuszkovicz et al. ................ 546/86
4,435,403 3/1984 Braestrup et al. .................... 546/86

Primary Examiner—Henry H. Jiles
Assistant Examiner—J. Richter
Attorney, Agent, or Firm—Millen & White

[57] ABSTRACT

New β-carboline-3-carboxylic acid esters have the general formula I:

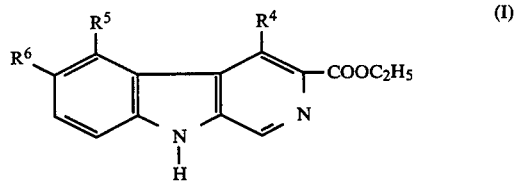

wherein $R^4$, $R^5$ and $R^6$ have specified meanings.

The new compounds exhibit surprising psychotropic properties.

12 Claims, No Drawings

β-CARBOLINE-3-CARBOXYLIC ACID DERIVATIVES, AND THEIR USE AS PSYCHOTROPIC AGENTS

BACKGROUND OF THE INVENTION

This invention relates to new β-carboline-3-carboxylic acid derivatives. These new compounds possess valuable pharmacological properties which make them useful in psychopharmaceutical preparations.

EP Patent publications Nos. 30254 and 54507 disclose related β-carbolines having pharmacological properties. See also U.S. Pat. Nos. 4,371,536 and 4,435,403.

SUMMARY OF THE INVENTION

It is an object of this invention to provide new β-carbolines having valuable pharmacological properties.

Upon further study of the specification and appended claims, further objects and advantages of this invention will become apparent to those skilled in the art.

These objects have been achieved by providing β-carboline-3-carboxylic acid esters of the formula I

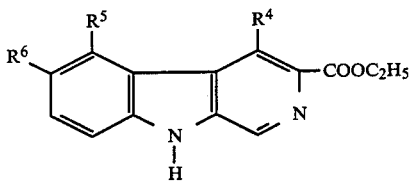

wherein
$R^4$ is methyl, ethyl or methoxymethyl,
$R^5$ is hydrogen, $-OR^8$ (wherein $R^8$ is $C_{1-4}$-alkyl or $C_{3-7}$-cycloalkyl, $C_{4-7}$-alkylcycloalkyl, propinyl or cyclohexenyl), or $-CH_2-OR^9$, wherein $R^9$ is $C_{1-4}$-alkyl,
$R^6$ is hydrogen, $-OR^{10}$ (wherein $R^{10}$ is straight or branched $C_{1-4}$-alkyl or $C_{3-6}$-cycloalkyl) or $-CH_2-OR^9$, wherein $R^9$ has the meaning given above,
with the proviso that,
$R^5$ and $R^6$ are not both hydrogen, and
$R^5$ is not isopropoxy or ethoxymethyl when $R^4$ is methyl.

DETAILED DISCUSSION

The term $C_{1-4}$-alkyl in all occurrences includes alkyl groups with up to 4 carbon atoms, e.g., methyl, ethyl, iso-propyl, n-propyl, n-butyl, isobutyl, sec-butyl, tert-butyl, etc. The terms cycloalkyl and alkylcycloalkyl include cyclopropyl, methylcyclopropyl, cyclobutyl, cyclopentyl, cyclohexyl and methylcyclohexyl.

Surprisingly, it has now been found that the compounds of this invention exhibit psychotropic properties which are clearly superior to those of the prior art compounds.

The superior psychotropic properties of the compounds of the invention are evidenced by their improved capacity for displacing radioactively labelled flunitrazepam from benzodiazepine receptors.

It is well known (Squires, R. F. and Braestrup, C., Nature (London) 266 (1977) 734)) that specific sites in the central nervous systems of vertebrates exhibit a high specific affinity for binding the 1,4- and 1,5-benzodiazepines. These sites are called benzodiazepine receptors.

The displacement activity of the compounds of the invention has been determined by determining the $IC_{50}$ value and $ED_{50}$ value.

The $IC_{50}$ value represents the concentration which causes a displacement of 50% of the specific binding of $^3H$-flunitrazepam (1.0 nM, 0° C.) in samples comprising a total volume of 0.55 ml of a suspension of brain membrane, e.g. from rats.

The displacement test is performed as follows:

0.50 ml of a suspension of non-treated rat forebrain in 25 mM $KH_2PO_4$, pH=7.1 (5–10 mg tissue/sample) is incubated for 40–60 minutes at 0° C. together with $^3H$-diazepam (specific activity 87 Ci/mmol, 1.0 nM). After incubation the suspension is filtered through "Whatman GF/C" glass fiber filters, the residue washed twice with cold buffer solution and the radioactivity measured by scintillation counting.

The test is repeated except that prior to the addition of the radioactively labelled benzodiazepine, a given amount or an excessive amount of the compound, the displacement capability of which is to be determined, is added. Based on the data obtained, the $IC_{50}$ value can be calculated.

The $ED_{50}$ value represents the dose (mg/kg) of a test substance which causes the specific binding of flunitrazepam to benzodiazepine receptors in a living brain to be reduced to 50% of the control value. Such an in vivo test is carried out as follows:

Groups of mice are injected with the test substance of different doses and usually subcutaneously. 15 minutes later $^3H$-flunitrazepam is administered intravenously to the mice, and after a further 20 minutes, the mice are killed. Their forebrain membranes are removed and the radioactivity of these forebrain membranes is measured by scintillation counting. The $ED_{50}$ value is determined from dose-response curves.

Test results obtained by testing some compounds of the invention will appear from the following Table I:

TABLE I

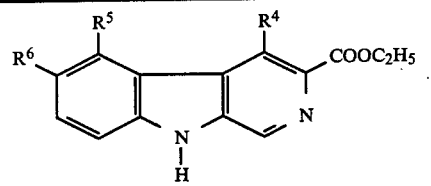

| | | | Inhibition of $H^3$—flunitrazepam binding | |
| | | | in vitro $IC_{IC}$ | in vivo $ED_{50}$ |
| $R^4$ | $R^5$ | $R^6$ | ng/ml | mg/kg |
|---|---|---|---|---|
| $CH_2OCH_3$ | $-CH_2OC_2H_5$ | H | 0.4 | 2.4 |
| $CH_2OCH_3$ | −O−⟨ | H | 0.6 | 1.4 |
| $CH_2OCH_3$ | −O−◇ | H | 0.2 | 0.5 |

The compounds of this invention can be used for the formulation of pharmaceutical preparations, e.g for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salts for influencing osmostic pressure, buffers and/or coloring substances and the like, which do not deleteriously react with the active compounds.

Injectable solutions or suspensions, preferably aqueous solutions with the active compound dissolved in polyhydroxyethoxylated castor oil are particularly suitable for parenteral application.

Ampoules are conveniently unit dosages.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used, wherein a sweetened vehicle can be employed.

Generally, the compounds of this invention are dispensed in unit dosage form comprising 0.05-100 mg in a pharmaceutically acceptable carrier per unit dosage.

The dosage of the compounds according to this invention is 0.1-300 mg/day, preferably 0.5-30 mg/day, when administered to patients, e.g. humans, as a drug.

All compounds of this invention have affinity for benzodiazepine receptors. Consequently, they have a spectrum of the activities of the benzodiazepines, e.g., muscle relaxant, sedative, anxiolytic or anticonvulsant and are useful for the conventional corresponding indications, e.g., as muscle relaxants, antiepileptics, sedatives, hypnotics, tranquilizers, etc. These activities can be from agonistic to antagonistic to inverse agonistic, the corresponding indications being conventional in each case, e.g., antagonistically they can be used to reverse benzodiazepine effects, e.g., in cases of overdose, inverse agonistically they can be used to achieve the inverse effects of the benzodiazepines, e.g., they can be used as vigilance enhancers, etc. The type and level of activity for a given dosage of each compound can be conventionally determined by routine experimentation using well known pharmacological protocols for each of the activities; the corresponding indications treatable at that dosage will be well known to skilled workers based on the pharmacological results. The compounds of this invention are particularly noteworthy for their anxiolytic, anticonvulsant and nootropic activity, e.g., to treat anxiety, epilepsy and vigilance or cognitive deficiencies at the above dosages by analogy to the known agent diazepam or peracetam.

The compounds of the invention may be prepared by cyclization of an indol derivative of formula II

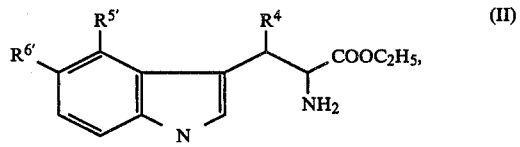

wherein
$R^4$ is methyl, ethyl or methoxymethyl,
$R^{5'}$ is hydroxy, hydrogen, —$OR^8$ (wherein $R^8$ is $C_{1-4}$-alkyl or $C_{4-7}$-cycloalkyl or -alkylcycloalkyl or propinyl or cyclohexenyl) or —$CH_2$—$O^9$, wherein $R^9$ is $C_{1-4}$-alkyl,
$R^{6'}$ is hydroxy, hydrogen, —$OR^{10}$ (wherein $R^{10}$ is branched $C_{1-4}$-alkyl or $C_{3-6}$-cycloalkyl) and —$CH_2$—$OR^9$, wherein $R^9$ has the meaning given above, with glyoxylic acid or formaldehyde to form the corresponding 1,2,3,4-tetrahydrocarboline compound, dehydrogenating said 1,2,3,4-tetrahydrocarboline compound to form the corresponding β-carboline-3-carboxylic acid ethylester and, if $R^{5'}$ or $R^{6'}$ is OH, etherifying said hydroxy group by reaction with a compound of the general formula III

RX (III), wherein R is $C_{1-4}$-alkyl, $C_{4-7}$-cycloalkyl or -alkylcycloalkyl, propinyl or cyclohexenyl and X is chlorine or bromine.

The starting materials in this process are all known or readily preparable from known substances using fully conventional processes; see, e.g., U.S. Pat. No. 4,435,403.

The process of this invention is conducted according to procedures and under conditions known to those of skill in the art; see, e.g., U.S. Pat. No. 4,371,536 and U.S. Pat. No. 4,435,403.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-Ethoxymethyl-4-methoxymethyl-β-carboline-3-carboxylic acid ethylester 1,2,3,4-Tetrahydro-3-ethoxycarbonyl-5-ethoxymethyl-4-methoxymethyl-β-carboline-3-carboxylate (6.8 g) in xylene (1.1 l) is boiled under reflux for 1 hour. The xylene is evaporated in vacuo and the residue is dissolved in methylene chloride (b 600 ml). 2,3-Dichloro-5,6-dicyano-p-benzoquinone (4.5 g) is added in one portion to the ice-cooled solution. After 5 minutes stirring the solution is washed with 1.2 vol. % of aqueous ammonia, and the methylene chloride is removed by distillation in vacuo. The residue, after two chromatographies on silicagel, first with a mixture of methylene chloride and acetone (1:1), and then with a mixture of methylene chloride and methanol (95:5) yields 0.46 g of pure 5-ethoxymethyl-4-methoxymethyl-β-carboline-3-carboxylic acid ethylester. M.p. 94°97° C.

The starting material 1,2,3,4-tetrahydro-3-ethoxycarbonyl-5-ethoxymethyl-4-methoxymethyl-β-carboline-3-carboxylate was prepared as follows:

(A) 4-Ethoxymethylindole

A solution of 4-hydroxymethylindole (14.8 g) in methylene chloride (300 ml) was concentrated in vacuo to a volume of 200 ml. Under an atmosphere of nitrogen, the solution was cooled to —4° C. A solution of N-ethyldiisopropylamine (14.2 g) in methylene chloride (130 ml) kept at a temperature of 10° C. was added within half an hour.

Triethyloxonium-tetrafluoroborate (20.9 g) dissolved in methylene chloride (140 ml) cooled to 10° C. was added to the reaction mixture within one hour. The temperature raised to −1° C. The mixture was stirred at this temperature for one hour. Then it was allowed to warm to room temperature and stirred for another 18 hours.

Next, the reaction mixture was treated 3 times with a saturated aqueous solution of sodium bicarbonate (300 ml), then once with 0.5n hydrochloric acid (220 ml), and, finally, once with water (300 ml).

After evaporation of the solvent, the crude product was purified by chromatography on silicagel with cyclohexane/ethylacetate (4:1).

Yield: 14 g 4-ethoxymethylindole, m.p. 50°–52° C.

(B) Ethyl-3-(4-ethoxymethylindol-3-yl)-4-methoxy-2-nitrobutyrate

Under an argon atmosphere acetic acid (33.1 ml) was added to a solution of 4-ethoxymethylindole (5.1 g) and ethyl-3-hydroxy-4-methoxy-2-nitrobutyrate (7 ml) in toluene (200 ml). The mixture was refluxed for two hours and a second portion of ethyl-3-hydroxy-4-methoxy-2-nitrobutyrate (7 ml) was added. After another two hours of refluxing, the solvent and all volatiles were evaporated in vacuo.

The residue was dissolved in ethylacetate, the solution, after treatment with water, yielded a crude product which was purified by chromatography on silicagel with methylene chloride.

1.1 g of pure ethyl-3-(4-ethoxymethylindol-3-yl)-4-methoxy-2-nitrobutyrate, m.p. 118°–120° C., was obtained.

(C) Ethyl-2-amino-3-(4-ethoxymethylindol-3-yl)-4-methoxybutyrate

Ethyl-3-(4-ethoxymethylindol-3-yl)-4-methoxy-2-nitrobutyrate (11.1 g) in ethanol (350 ml) was catalytically hydrogenated with Raney-nickel at room temperature under atmospheric pressure. The product obtained after filtration of the catalyst and evaporation of the solvent, was dissolved in a mixture of diethylether and ethylacetate. The solution was treated with water and evaporated. 8 g of oily ethyl-2-amino-3-(4-ethoxymethylindol-3-yl)-4-methoxybutyrate were obtained.

(D) 1,2,3,4-Tetrahydro-3-ethoxycarbonyl-5-ethoxymethyl-4-methoxymethyl-β-carboline-3-carboxylate Under an argon atmosphere, solutions of ethyl-2-amino-3-(4-methoxymethylindol-3-yl)-4-methoxybutyrate (7.9 g) in ethylacetate (46 ml) and glyoxylic acid monohydrate (2.3 g) in water (31 ml) were mixed. By addition of potassium hydrogencarbonate the pH of the mixture was raised to 4. It was stirred vigorously for 18 hours. Then the ethylacetate was evaporated. The aqueous solution was extracted repeatedly with ethylacetate. The extracts and the original solution were combined and washed with water. On evaporation, the solution yielded 6.9 g of 1,2,3,4-tetrahydro-3-ethoxycarbonyl-5-ethoxymethyl-4-methoxymethyl-β-carboline-3-carboxylate, an orange foam, proved pure by thin layer chromatography.

EXAMPLE 2

Ethyl 5-isopropoxy-4-methoxymethyl-β-carboline-3-carboxylate 0.3 g ethyl 5-hydroxy-4-methoxymethyl-β-carboline-3-carboxylate is refluxed for 3 hours in 30 ml dimethylformamide under nitrogen with 0.3 g potassium carbonate and 0.149 g (0.115 ml) 2-bromopropane. Following filtration and evaporation under vacuum, the residue is purified by chromatography on silica gel (methylene chloride+ethanol, 1000:25).

Yield: 0.173 g ethyl 5-isopropoxy-4-methoxymethyl-β-carboline-3-carboxylate, m.p. 230°–231° C. (decomposition).

EXAMPLE 3

Ethyl 5-cyclobutoxy-4-methoxymethyl-β-carboline-3-carboxylate

Ethyl 5-cyclobutoxy-4-methoxymethyl-β-carboline-3-carboxylate, m.p. 196°–197° C., is prepared from 5-hydroxy-4-methoxymethyl-β-carboline-3-carboxylic acid ethylester and cyclobutylbromide by a method which is analogous to the method described above.

EXAMPLE 4

In analogous manner the following compounds are prepared:
(a) Ethyl 5-cyclopropylmethyloxy-4-methoxymethyl-β-carboline-3-carboxylate, F. 141°–142° C.;
(b) Ethyl 4-methoxymethyl-5-propionyloxy-β-carboline-3-carboxylate, F. 149°–150° C.;
(c) Ethyl 6-ethoxymethyl-4-methyl-β-carboline-3-carboxylate, F. 174°–175° C.;
(d) Ethyl 6-ethoxymethyl-4-methoxymethyl-β-carboline-3-carboxylate, F. 141°–142° C.;
(e) Ethyl 6-isopropoxy-4-methoxymethyl-β-carboline-3-carboxylate, F. 140° C. (decomposition);
(f) Ethyl 6-cyclopentyloxy-4-methoxymethyl-β-carboline-3-carboxylate, F. 80° C.;
(g) Ethyl 6-isopropoxy-4-methyl-β-carboline-3-carboxylate, F. 237°–238° C.;
(h) Ethyl 4-ethyl-6-isopropoxy-β-carboline-3-carboxylate, F. 204°–205° C.;
(i) Ethyl 5-cyclopentyloxy-4-methoxymethyl-β-carboline-3-carboxylate, F. 238°–240° C.;
(j) Ethyl 5-cyclohexylmethoxy-4-methoxymethyl-β-carboline-3-carboxylate, oily substance;
(k) Ethyl 4-methoxymethyl-4-n-propoxy-β-carboline-3-carboxylate, F. 193°–195° C.;
(l) Ethyl 5-(2-cyclohexenyloxy)-4-methoxymethyl-β-carboline-3-carboxylate, F. 198°–200° C.;
(m) Ethyl 5-isobutoxy-4-methoxymethyl-β-carboline-3-carboxylate, F. 209°–210° C.;
(n) Ethyl 5-(2-butoxy)-4-methoxymethyl-β-carboline-3-carboxylate, F. 233°–234° C.;
(o) Ethyl 4-ethyl-5-n-propoxy-β-carboline-3-carboxylate, F. 140°–143° C.;
(p) Ethyl 5-cyclobutoxy-4-ethyl-β-carboline-3-carboxylate, F. 260°–263° C.;
(q) Ethyl 4-methyl-5-(1-methylpropoxy)-β-carboline-3-carboxylate, F. 116°–118° C.;
(r) Ethyl 4-methyl-5-n-propoxy-β-carboline-3-carboxylate, F. 173°–174° C.; and
(s) Ethyl 5-cyclopentyloxy-4-methyl-β-carboline-3-carboxylate, F. 165° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A β-carboline-3-carboxylic acid ester of the formula

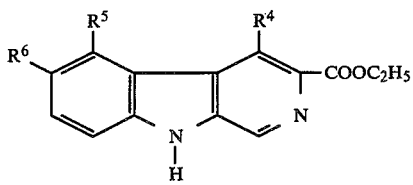

(I)

wherein $R^4$ is methyl, ethyl or methoxymethyl, $R^5$ is $-OR^8$ $R^8$ is $C_{3-7}$-cycloalkyl, $C_{4-7}$-alkylcycloalkyl, propinyl or cyclohexenyl, $R^9$ is $C_{1-4}$-alkyl, $R^6$ is hydrogen, $-OR^{10}$, or $-CH_2-OR^9$, $R^{10}$ is $C_{1-4}$-alkyl or $C_{3-6}$-cycloalkyl.

2. A β-carboline-3-carboxylic acid ester of the formula

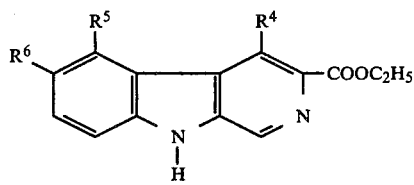

wherein $R^4$ is methyl, ethyl or methoxymethyl, $R^5$ is hydrogen, $-OR^8$, or $-CH_2-OR^9$ $R^8$ is $C_{1-4}$-alkyl, $C_{3-7}$-cycloalkyl, $C_{4-7}$-alkylcycloalkyl, propinyl or cyclohexenyl, $R^9$ is $C_{1-4}$-alkyl $R^6$ is $-OR^{10}$ and $R^{10}$ is cycloalkyl, with the provisos that, $R^5$ is not isopropoxy or ethoxymethyl when $R^4$ is methyl.

3. A compound of claim 1, wherein $R^4$ is methoxymethyl.

4. A compound of claim 1, wherein $R^6$ is H.

5. A compound of claim 3, wherein $R^6$ is H.

6. Ethyl 4-methoxymethyl-5-cyclobutoxy-β-carboline-3-carboxylate, a compound of claim 1.

7. A pharmaceutical composition comprising a psychotropically effective amount of a compound of claim 1 and a pharmaceutically acceptable carrier.

8. A composition of claim 7, wherein the amount of said compound is 0.05–100 mg.

9. A pharmaceutical composition comprising a psychotropically effective compound of claim 2 and a pharmaceutically acceptable carrier.

10. A composition of claim 9, wherein the amount of said compound is 0.05–100 mg.

11. A method of achieving a psychotropic effect in a patient comprising administering to the patient a psychotropically effective amount of a compound of claim 1.

12. A method of achieving a psychotropic effect in a patient comprising administering to the patient a psychotropically effective amount of a compound of claim 1.

* * * * *

UNITED STATES PATENT AND TRADEMARK OFFICE
CERTIFICATE OF CORRECTION

PATENT NO.   :   4,631,285
DATED        :   December 23, 1986
INVENTOR(S)  :   Erling Niels Petersen et al It is certified that error appears in the above-identified patent and that said Letters Patent is hereby corrected as shown below:

Column 8, claim 2, line 17:   reads "$R^{10}$ is cycloalkyl."

should read "$R^{10}$ is $C_{3-6}$-cycloalkyl."

Signed and Sealed this

Twenty-fourth Day of November, 1987

Attest:

DONALD J. QUIGG

Attesting Officer

Commissioner of Patents and Trademarks